United States Patent [19]

Carter et al.

[11] 4,250,171
[45] Feb. 10, 1981

[54] PEST CONTROL

[75] Inventors: Stuart W. Carter, Berkhamsted; Peter R. Skidmore, Tring, both of England

[73] Assignee: Burroughs Wellcome Co., Research Triangle Park, N.C.

[21] Appl. No.: 36,538

[22] Filed: May 7, 1979

Related U.S. Application Data

[63] Continuation of Ser. No. 887,934, Mar. 17, 1978, abandoned.

[30] Foreign Application Priority Data

Mar. 18, 1977 [GB] United Kingdom ............... 11504/77

[51] Int. Cl.³ .................... A01N 37/34; A01N 65/00
[52] U.S. Cl. ..................................... 424/189; 424/304
[58] Field of Search ............................ 424/304, 189; 260/465 D

[56] References Cited

FOREIGN PATENT DOCUMENTS 14134191 12/1975 United Kingdom .

Primary Examiner—Stanley J. Friedman
Attorney, Agent, or Firm—Donald Brown

[57] ABSTRACT

A method for controlling pests of the order Coleoptera in stored agricultural produce comprising the application of a compound of formula

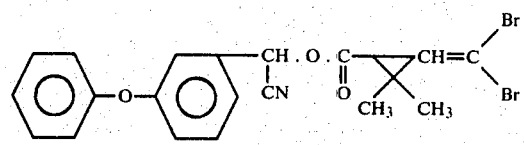

to the pest or to the produce.

9 Claims, No Drawings

PEST CONTROLsp

This is a continuation of application Ser. No. 887,934 filed Mar. 7, 1978, now abandoned.

This invention relates to the use of known compounds and pesticidal formulations containing them for controlling insect infestation of stored agricultural produce. Such insects include beetles of the Order Coleoptera.

A variety of insecticides have been shown to be active against such beetles, including the natural extracts of the pyrethrum flower, called pyrethrins. Later synthetic pyrethrin-like esters, called pyrethroids, were synthesized and then found to be active. However, although several new pyrethroids have shown valuable activity against many species of arthropods in both the animal health and crop protection fields, they exhibit only moderate activity against grain pests of the genus Tribolium. Such pyrethroids include bioresmethrin, resmethrin, phenothrin, and fenvalerate. Similarly natural pyrethrins have only moderate activity against Tribolium spp. These pyrethroids are active against other grain pests within the order Coleoptera, for example Sitophilus spp., at levels much below those necessary for controlling Tribolium spp. An example of this differential toxicity is bioresmethrin as outlined in Table 1.

Compounds of formula (I):

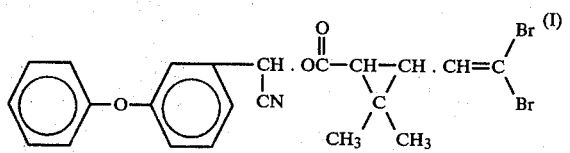

are knowwn from U.K. Pat. Nos. 1,413,491 and 1,448,228 to possess insecticidal activity.

It has now been found by the applicants that the compounds of formula (I) are substantially more active against the grain pest Tribolium castaneum than other pyrethroids evaluated hereto.

The structural formula (I) is intended to cover all geometric and optical isomers of the compound including the (+)-cis-isomer, the (+)-trans-isomer, the (+)-trans-isomer, the (+)-cis-isomer and the (+)-cis, trans-isomer (the stereochemistry referring to that of the cyclopropane ring); moreover the alcohol moiety of the compound of formula (I) may be selected from the (−)-isomer, the (+)-isomer and the (+)-isomer.

The preferred isomer is (−)-α-cyano-3-phenoxybenzyl-(+)-cis-2,2-dimethyl-3-(2,2-dibromovinyl)cyclopropane-1-carboxylate(decamethrin).

The compounds of formula (I) are active against grain pests of the order Coleoptera and especially those of the genera. Tribolium, Sitophilus, Oryzaephilus and Rhizopertha, particularly the species T. castaneum, T. confusum, S. granarius, S. oryzae, S. zaemais, R. dominica, O. surinamensis and O. mercator.

The compounds of formula (I) may be made more effective by the inclusion of a synergist, in particular piperonyl butoxide.

The compounds of formula (I), with or without the addition of a synergist may be used alone or may be formulated into a pesticidal formulation by admixture with a carrier which may take the form of one or more of the following: wetting, diluent, surface active, emulsifying, dispersing and thickening agents, a solvent, an antioxidant or other standard carrier ingredients used when formulating insecticides.

Liquid or semi-liquid formulations which may be used include miscible-oils with or without an organic solvent, for application by spraying as a water-based emulsion. Solid formulations include dusts, powders and granules for dilution prior to use with solid inerts. Possible solid diluents are, for example, Kaolin, powdered chalk, talcs, kieselguhr, dolomite, calcium carbonate, powdered magnesia, Fuller's earth, gypsum, Hewitt's earth, diatomaceous earth, china clay, bentonite and other colloidal clays. Organic carriers which may be used include lactose, offal sharps and other similar finely ground vegetable products. Water dispersible powder formulations may be used comprising a wetting agent to facilitate the dispersion of the powder in water.

The preparations thus formed after dilution with water if appropriate may then be applied to the grain by spraying, dusting, or other forms of admixture. Air may also be used as both a carrier and an inert diluent simultaneously, for application of the formulation to the grain either as a fog, mist or cloud.

The formulations of the present invention with or without dilution may be applied to the grain so that the grain may contain from 0.01 ppm to 10 ppm of the compound of formula (I) with or without the addition of 0.01 ppm to 100 ppm of a pyrethroid synergist.

It will be appreciated from the foregoing that what we will claim may comprise any novel feature described herein, principally and not exclusively, for example:

(a) A method of controlling pests of the order Coleoptera in stored agricultural produce comprising the application to the pests or to the produce of a compound as defined in formula (I) hereinbefore, optionally with a synergist for said compound; and (b) A method of controlling pests of the order Coleoptera in stored agricultural produce comprising the application to the pests or to the produce of a formulation containing:

(i) a compound as defined in formula (I) hereinbefore,
(ii) an acceptable carrier therefor, and optionally
(iii) a synergist for said compound.

EXAMPLE 1

Miscible-oil formulations containing decamethrin, permethrin or bioresmethrin with or without the addition of piperonyl butoxide at a defined ratio of 1:2.5, were prepared and emulsions of various concentrations were made up by dilution with the required volume of water.

3 Kg. batches of insecticide-free wheat grain were sprayed with the emulsions. 100 g. samples of the treated wheat were then infested with thirty S. granarius and fifty T. castaneum beetles. The concentration required to kill half and 95% of the beetles were respectively determined as the LC50 and LC 95 values.

The results are illustrated in Table 1 where it can be seen that in comparison with permethrin or bioresmethrin, decamethrin is substantially equitoxic to both S. granarius and T. castaneum.

TABLE 1

| | Apparent LC50 LC95 (ppm) at indicated times of sampling after spraying. | | | | | |
|---|---|---|---|---|---|---|
| S. granarius | 6 days | 14 days | 1 m | 3 m | 6 m | 10 months |

TABLE 1-continued

| S. granarius | | Apparent LC50 LC95 (ppm) at indicated times of sampling after spraying | | | | | |
|---|---|---|---|---|---|---|---|
| | | 6 days | 14 days | 1 m | 3 m | 6 m | 10 months |
| Bio-resmethrin + pb* (1:2.5) | LC50 | 0.10 | 0.75 | 0.96 | 1.1 | 1.35 | 1.90 | 2.40 |
| | LC95 | 2.30 | 1.70 | 1.85 | 4.10 | 4.00 | 5.10 |
| Permethrin | LC50 | 1.60 | — | — | 1.0 | — | — |
| | LC95 | 2.48 | — | — | 1.75 | — | — |
| Permethrin + pb (1:2.5) | LC50 | 1.02 | — | — | 0.90 | — | — |
| | LC95 | 1.60 | — | — | 1.40 | — | — |
| Decamethrin | LC50 | 0.18 | 0.20 | 0.27 | 0.20 | 0.14 | 0.40 |
| | LC95 | 0.60 | 0.60 | 0.58 | 0.47 | 0.60 | 0.74 |
| Decamethrin + pb* (1:2.5) | LC50 | 0.13 | 0.13 | 0.15 | 0.20 | 0.12 | 0.10 |
| | LC95 | 0.21 | 0.17 | 0.36 | 0.27 | 0.32 | 0.40 |
| T. centeneum | | | | | | | |
| Bio-resmethrin + pb* (1:2.5) | LC50 | 4.30 | 2.80 | 2.50 | 3.20 | 7.70 | — |
| | LC95 | 10.00 | 8.60 | 7.50 | 10.25 | 13.30 | — |
| Permethrin | LC50 | 2.80 | — | — | 3.80 | — | — |
| | LC95 | 3.50 | — | — | 10.30 | — | — |
| Permethrin + pb* (1:2.5) | LC50 | 1.21 | — | — | 2.80 | — | — |
| | LC95 | 1.54 | — | — | 5.00 | — | — |
| Decamethrin | LC50 | 0.28 | 0.23 | 0.23 | 0.19 | 0.16 | — |
| | LC95 | 0.58 | 0.40 | 0.39 | 0.36 | 0.34 | — |
| Decamethrin + pb* (1:2.5) | LC50 | 0.13 | 0.10 | 0.11 | 0.13 | 0.12 | — |
| | LC95 | 0.20 | 0.17 | 0.21 | 0.17 | 0.46 | — |

| EXAMPLE 2 | Miscible Oil Formulations | | |
|---|---|---|---|
| | (a) w/w | (b) w/w | (c) w/w |
| Decamethrin | 1.32% | 1.3% | 13.0% |
| Piperonyl butoxide | 3.30 | 13.0 | 13.0 |
| Antioxidants | 1.32 | 2.6 | 6.5 |
| Emulsifier | 20.00 | 20.0 | 20.0 |
| Xylene | 74.06 | 63.1 | 47.5 |
| | 100.00 | 100.0 | 100.0 |

When the diluted formulation is applied to the grain at a dilution rate as specified below, and at an application rate of 1 liter to every 1175 kgs. grain, the estimated deposits on the grain are:

| | (a) | (b) | (c) |
|---|---|---|---|
| Dilution Rate | 1 + 1000 | 1 + 19 | 1 + 9 |
| Decamethrin,ppm | 0.01 | 0.5 | 10.0 |
| Piperonyl butoxide,ppm | 0.025 | 5.0 | 10.0 |
| Antioxidant,ppm | 0.01 | 1.0 | 5.0 |

| EXAMPLE 3 | Wettable Powder Formulations | | |
|---|---|---|---|
| | (a) w/w | (b) w/w | (c) w/w |
| Decamethrin | 1.2% | 1.2% | 12.0% |
| Piperonyl butoxide | 3.0 | 12.0 | 12.0 |
| Antioxidant | 1.2 | 1.2 | 6.0 |
| Wetting Agent | 0.5 | 0.5 | 0.5 |
| Dispersing agent | 2.0 | 2.0 | 3.0 |
| Diatomaceous earth | 92.1 | 83.1 | 66.5 |
| | 100.0 | 100.0 | 100.0 |

When the diluted formulation is applied to the grain at a dilution rate as specified below, and at an application rate of 1 liter to every 1175 kgs. grain, the estimated deposits on the grain are:

| | (a) | (b) | (c) |
|---|---|---|---|
| Dilution Rate | 1 + 1000 | 1 + 19 | 1 + 9 |
| Decamethrin,ppm | 0.01 | 0.5 | 10.0 |
| Piperonyl butoxide,ppm | 0.025 | 5.0 | 10.0 |
| Antioxidant,ppm | 0.01 | 0.05 | 5.0 |

What we claim is:

1. A method of controlling the pest *Tribolium castaneum* in stored agricultural produce infected with said pest comprising the application of a pesticidally effective amount of a compound of formula $$\text{C}_6\text{H}_5\text{-O-C}_6\text{H}_4\text{-CH(CN).O.C(=O)-}\underset{\underset{\text{H}_3\text{C}\ \ \text{CH}_3}{}}{\triangle}\text{-CH=CBr}_2$$

to the pest or to the infected produce.

2. A method according to claim 1 wherein the compound is (−)-α-cyano-3-phenoxybenzyl-(+)-cis-2,2 dimethyl-3-(2,2-dibromovinyl)cyclopropane-1-carboxylate.

3. A method according to claim 1 wherein (−)-α-cyano-3-phenoxbenzyl-(+)-cis-2,2-dimethyl-3-(2,2-dibromovinyl)cyclopane-1-carboxylate is applied to *Tribolium castaneum* or to the produce.

4. A method according to claim 1 wherein a formulation comprising said compound in admixture with a carrier or diluent is applied.

5. A method according to claim 4 wherein said formulation is in the form of a water-based emulsion prepared from a miscible-oil or wettable-powder preparation.

6. A method according to claim 1 wherein piperonyl butoxide, a pyrethroid synergist, is also applied.

7. A method according to claim 6 wherein from 0.01 ppm to 10 ppm of said compound optionally with from 0.01 ppm to 100 ppm of a pyrethroid synergist is applied to the grain.

8. The method of controlling *T. castaneum* beetles which comprises applying an effective amount of a compound of the formula $$\text{C}_6\text{H}_5\text{-O-C}_6\text{H}_4\text{-CH(CN).O.C(=O)-}\underset{\underset{\text{CH}_3\ \ \text{CH}_3}{}}{\triangle}\text{-CH=CBr}_2$$

to the beetles.

9. The method of claim 8 in which the compound is (−)-α-cyano-3-phenoxybenzyl-(+)-cis-2,2, dimethyl-3-(2,2-dibromovinyl)cyclopropane-1-carboxylate.

* * * * *